(12) United States Patent
Della Valle et al.

(10) Patent No.: US 8,288,361 B2
(45) Date of Patent: Oct. 16, 2012

(54) PHARMACEUTICAL COMPOSITIONS FOR THE TREATMENT OF ULCERATIONS

(75) Inventors: Francesco Della Valle, Padua (IT); Maria Federica Della Valle, Padua (IT)

(73) Assignee: Innovet Italia S.r.l., Milan (IT)

( * ) Notice: Subject to any disclaimer, the term of this patent is extended or adjusted under 35 U.S.C. 154(b) by 354 days.

(21) Appl. No.: 11/406,852

(22) Filed: Apr. 19, 2006

(65) Prior Publication Data

US 2006/0257510 A1 Nov. 16, 2006

(30) Foreign Application Priority Data

Apr. 19, 2005 (EP) .................................. 05425242

(51) Int. Cl.
*A01N 43/04* (2006.01)
*A61K 31/715* (2006.01)
(52) U.S. Cl. ........................................................ 514/54
(58) Field of Classification Search .................... None
See application file for complete search history.

(56) References Cited

U.S. PATENT DOCUMENTS 5,288,479 A * 2/1994 Gorman et al. ................. 424/49
6,964,783 B1 * 11/2005 Shrivastava ................... 424/725
2010/0191219 A1 7/2010 Gupta et al.

FOREIGN PATENT DOCUMENTS

| EP | 0 550 006 A2 | 7/1993 |
| EP | 0 599 188 A1 | 6/1994 |
| EP | 1 374 903 A1 | 1/2004 |
| WO | 96/03973 | 2/1996 |
| WO | WO 00/74668 A1 | 12/2000 |
| WO | 01/04083 A1 | 1/2001 |
| WO | 01/10402 A1 | 2/2001 |

OTHER PUBLICATIONS

Chemical Abstracts Registry Descrption, 2006.*
Anonymous, Restomyl (Mucoadhesive Odontostomatological gel): INNOVET, Internet: URL:http://web.archive.org/web/20040205183035/http://www.innovet.it/reactive-english/restomyl.html, Sep. 2005.
R.A. Cutting, "Chronic Leg Ulcers—Treatment with Unna's Paste Boot." The American Journal of Surgery, New Series, vol. 8, No. 4, pp. 743-749, Apr. 1930.

* cited by examiner

*Primary Examiner* — Layla Bland
(74) *Attorney, Agent, or Firm* — Dickstein Shapiro LLP

(57) ABSTRACT

The present invention relates to a pharmaceutical composition, for human and veterinary use, that may be used to induce, potentiate and normalise the various phases of the tissue repair process triggered following ulceration and wounding—either involving the loss of matter or not—of neurogenic, vasogenic or traumatic origin, even in cases where the lesions are directly or indirectly associated with underlying systemic pathologies.

Particularly, the present invention relates to a pharmaceutical composition comprising an N-acyl derivative of an amino alcohol belonging to the ALIAmides class of molecules, a polyhydroxy alcohol and trans-traumatic acid or a derivative thereof.

21 Claims, No Drawings

PHARMACEUTICAL COMPOSITIONS FOR THE TREATMENT OF ULCERATIONS

FIELD OF THE INVENTION

The present invention relates to a pharmaceutical composition, for human and veterinary use, that may be used to induce, potentiate and normalise the various phases of the wound-healing process triggered following ulceration and wounding—either involving the loss of matter or not—of neurogenic, vasogenic or traumatic origin, even in cases where the lesions are directly or indirectly associated with underlying systemic pathologies.

BACKGROUND ART

It is known that scar formation is a fibroproliferative tissue response which, depending on the tissue or organ involved, results in the regeneration of the damaged tissue, or in the formation of a fibrotic scar. In addition, cutaneous/mucosal scar formation is an interactive process involving soluble mediators, extracellular matrix components, resident cells (keratinocytes, endothelial cells, fibroblasts and nerve fibres), infiltrating leukocytes, participating differentially and in strict temporal sequence towards the three phases of the scar formation process: inflammation, granulation (tissue formation or proliferative phase) and tissue remodelling.

Hence, the repair process is a dynamic and continuous phenomenon, given that the three phases are temporally coexistent with one another. For example, the inflammatory phase, fundamental for triggering the repair process, initiates abruptly at the instant of tissue damage, but persists both during cutaneous/mucosal re-epithelialisation, and during tissue remodelling (even though with different cellular components with respect to the acute phase), influencing both the catabolic and anabolic processes of the entire repair phenomenon.

Accordingly, the conceptual distinction of the repair process into three phases is only really useful for describing the events, sequentially linked to one another, in terms of the chemical mediators released locally at the site of the lesion, and the cellular components involved. Furthermore, the above distinction is useful for identifying during which phase and depending on which cellular elements and/or soluble mediators, any potential anomalies intervene. For example, such anomalies may relate to: excessive or defective chemotropism and/or the activation of specific cellular stipes at the site of the injury; excessive or defective release of soluble mediators; excessive or defective deposition and/or degradation of extracellular matrix; persistent fibroblastic hyperplasia; persistent microbial contamination, with chronicisation of the inflammatory phase. All the conditions listed above are clinically recognisable as hyper-reactivity and/or hyporeactivity of the tissue repair process in any of its phases, with consequential retardation of the sequentiality of the events and/or blockage of correct scar progression.

Pharmaceutical compositions which may be used in the treatment of ulcerations are known. However, these are not capable of providing a comprehensive treatment for ulcerations allowing rapid and efficient tissue repair. Without being bound to any particular theory, one possible cause may be that said compositions contain a factor which is active on one phase or on a single event within any given stage of the scar forming process, and hence they are not capable of addressing the above mentioned complex phenomena, in their entirety.

SUMMARY OF THE INVENTION

Therefore, the need for a pharmaceutical composition, capable of providing an adequate solution to the treatment of ulcerations and wounds, is still very much felt.

Hence, it is an object of the present invention a pharmaceutical composition for the treatment of ulcerations, such as defined in the annexed claims.

DETAILED DESCRIPTION OF THE INVENTION

It has been discovered that a pharmaceutical composition which is effective in the treatment of ulcerations and wounds contains a molecule of the so-called "ALIAmides" class (N-acyl derivatives of an aminoalcohol) as defined in claim 1 of European patent EP 0 550 006, together with a polyhydroxy alcohol and trans-traumatic acid (2-dodecenedioic acid) or a derivative thereof.

Preferably, the ALIAmide is adelmidrol, i.e. N, $N^1$-bis (2-hydroxyethyl) nonanediamide.

Preferably, the polyhydroxy alcohol is glycerol.

Without being bound to any particular theory, it has been observed that the composition of the invention is capable of:
  regulating, thanks to the presence of the ALIAmide, the degree of activation of the mast cells, both resident within and infiltrating the site of the lesion, through a central role in the coordination of the repair process, so as to modulate, through an inhibitory mechanism, the soluble mediators released in excess at the lesion site;
  ensuring the correct level of tissue hydration, so as to promote cell proliferation and differentiation and, whenever retarded, trigger the inflammatory phase;
  sustaining the lesion site re-epithelialisation phenomenon by potentiating keratinocyte advection.

It has been observed that the composition of the invention may preferably contain:
  (a) an agent capable of draining excess exudate, in order to prevent the amplification and persistence of inflammatory states that may be dangerous for the physiological consequentiality of the various scar-forming phases and premature cellular ageing, such agent preferably being a mucopolysaccharide or derivative thereof, more preferably sodium alginate; and/or
  (b) an agent capable of providing physiological extracellular matrix constituents, so as to provide and/or replenish guide molecules for the migration of resident cellular elements fundamental for tissue regeneration in the case of wounds and/or ulcers entailing dermal/connective tissue loss, such agent preferably being hyaluronic acid; and/or
  (c) an agent capable of controlling the behaviour of the contaminating microbial flora, both in proliferative terms and in terms of the release of extracellular matrix degrading enzymes, so as to counteract excess cellular activation and the development and/or progression of infectious states, because of easy invasiveness of the potential pathogen, said antimicrobial agent preferably being selected from *Echinacea purpurea* extract, deo-usnate (*Usnea barbata* extract), phytosphingosine and bronopol or mixtures thereof.

Preferably, the hyaluronic acid is in salt form. Even more preferably, it is in the form of a sodium or magnesium salt.

Advantageously, the hyaluronic acid and the trans-traumatic acid are in double salt form, such as magnesium hyaluronate trans-traumatate.

Preferably, the *Echinacea purpurea* extract will be a glycolic extract.

According to one preferred embodiment of the invention, the pharmaceutical composition will comprise (percentage by weight/total weight):

| | |
|---|---|
| an ALIAmide, preferably adelmidrol | 0.5-7% |
| a polyhydroxy alcohol, preferably glycerol | 30-60% |
| trans-traumatic acid | 0.02-1% |
| a mucopolysaccharide or derivative thereof, preferably sodium alginate | 0-5% |
| hyaluronic acid or a salt thereof (preferably, sodium salt) | 0-1% |
| *Echinacea purpurea* extract | 0-15% |
| *Usnea barbata* extract | 0-1% |
| phytosphingosine | 0-1% |
| bronopol | 0-0.2% |

Preferably, the composition of the invention will contain all the above listed active ingredients, i.e. the percentages of mucopolysaccharide, hyaluronic acid or salt thereof, *Echinacea purpurea* extract, *Usnea barbata* extract, phytosphingosine and bronopol will have values other than 0%.

The pharmaceutical compositions of the invention may be present in every suitable form for topical administration to the site of the wound, such as for example thickened solution, spray, foam, cream, gel, ointment, medicated gauze, polyacrylamide based or other pharmaceutically acceptable based dressing, etc. For this purpose, the composition may contain all those pharmaceutically acceptable additives which one skilled in the art may deem appropriate for the preparation of the desired composition, such as buffers, thickening agents, emulsifiers, diluents (distilled water), etc.

Surprisingly, the multifactorial modulation strategy of the scar-forming process which may be obtained through the association of the various active ingredients in the pharmaceutical compositions of the invention has proved to be significantly effective in restoring the correct consequentiality of the various phases of the healing process, both for severe wounds and, even more significantly, for healing ulcerations, characterised by loss of dermal/connective tissue and defined as chronic, since it is remaining unhealed for at least three weeks.

The compositions of the invention have demonstrated the capacity to reactivate the healing process in any anomalously temporally persistent wound-healing phase at the site of the lesion. The multifactorial wound-healing modulation strategy made possible by the present invention is hence effective in resolving the current chronicized tissue state, triggering and/or potentiating the scar-formation consequentially expected for the positive development of the tissue repair process.

Examples of ulcerations which may benefit from treatment with the pharmaceutical composition of the present invention are chronic ulcers with loss of cutaneous and sub-cutaneous tissue such as chronic diabetic ulcers in neuropathic or neurovascular patients, the venous and arterial ulcers in vasculopathic patients, pressure ulcers, bedsores, acute cutaneous and mucosal wounds resulting from thermal or physico-chemical trauma and surgical wounds.

Biological Activity

Table I shows the clinical results obtained from administration of the composition of the invention in gel form (Example 1) to patients affected by ulcerations of various kinds. 40 patients, with mean age of 65.9 years have been treated (14 male and 26 female patients). The treatment regimen has been the following: application of the gel twice daily following cleansing, for a period of 15 days.

Out of the 40 patients treated, 11 had vascular type ulceration, 10 traumatic, 10 diabetic, 3 lymphatic, 1 a burn and 5 had other types. The table shows the qualitative results (result "score": optimal, good, slight, null) assessed by the physician at the end of the treatment.

TABLE I

| | Ulcerative pathology (N° of Patients) | | | | | |
|---|---|---|---|---|---|---|
| | vascular | traumatic | diabetic | lymphatic | from a burn | others |
| Results | 11 | 10 | 10 | 3 | 1 | 5 |
| optimal | 6 | 5 | 5 | 2 | 1 | 4 |
| good | 3 | 2 | 4 | | | 1 |
| slight | 1 | 1 | 1 | 1 | | |
| null | 1 | 2 | | | | |

As may be observed from the data reported in the table, 50% to 100% of the patients (depending on the various types of ulceration) obtained results classified as optimal upon completion of treatment.

FORMULATION EXAMPLES

Example 1

Pharmaceutical Gel for Application onto Cutaneous Ulcers or Wounds 100 g of gel contains:

| | |
|---|---|
| glycerol | 40 g |
| *Echinacea purpurea* glycolic extract | 10 g |
| sodium alginate | 2.5 g |
| adelmidrol | 1 g |
| deo-usnate | 0.6 g |
| hyaluronic acid, sodium salt | 0.2 g |
| bronopol | 0.1 g |
| magnesium chloride 6 $H_2O$ | 0.1 g |
| phytosphingosine | 0.02 g |
| triethanolamine | 0.06 g |
| trans-traumatic acid | 0.06 g |

The invention claimed is:

1. A pharmaceutical composition comprising:
0.5-7 wt-% N,N$^1$-bis (2-hydroxyethyl) nonanediamide,
greater than 0 wt-% to 5 wt-% sodium alginate,
30-60 wt-% glycerol, and
0.02-1 wt-% trans-traumatic acid.

2. The composition according to claim 1, further comprising an agent including at least one physiological extracellular matrix component.

3. The composition according to claim 2, said agent comprising hyaluronic acid or a derivative thereof.

4. The composition according to claim 3, said hyaluronic acid derivative comprising the sodium or magnesium salt thereof.

5. The composition according to claim 1, further comprising an antimicrobial agent.

6. The composition according to claim 5, said antimicrobial agent being selected from the group consisting of *Echinacea purpurea* extract, *Usnea barbata* extract, phytosphingosine, bronopol and mixtures thereof.

7. The composition according to claim 6, wherein said *Echinacea purpurea* extract is a glycolic extract.

8. The composition according to claim 1, wherein the hyaluronic acid and the trans-traumatic acid are in the form of a double magnesium salt, magnesium hyaluronate trans-traumatate.

9. The composition according to claim 1, wherein the composition further comprises at least one of mucopolysaccharide, hyaluronic acid or a derivative thereof, *Echinacea purpurea* extract, *Usnea barbata* extract, phytosphingosine and bronopol are greater than 0%.

10. The composition according to claim 1, further comprising pharmaceutically acceptable additives selected from buffers, thickening agents, emulsifiers.

11. The composition according to claim 1 having a form adapted to topical administration.

12. The composition of claim 11, wherein composition is in the form of a thickened solution, a spray, a foam, an ointment, a cream, a gel, a medicated gauze, or a polyacrylamide based dressing.

13. A method of treating a disorder characterised by loss of dermal/connective tissue, the method comprising:
administering to a subject suffering from a disorder characterised by loss of dermal/connective tissue a pharmaceutical composition comprising the composition of claim 1.

14. The method of claim 13, wherein the disorder comprises acute wounds or scar forming ulcers.

15. The method of claim 13, wherein the disorder comprises chronic ulcerations.

16. The method of claim 13, wherein the disorder comprises chronic diabetic ulcers in neuropathic or neurovascular patients, venous or arterial ulcers in vasculopathic patients, pressure ulcers or bedsores, acute cutaneous or mucosal wounds resulting from thermal or physico-chemical trauma or surgical wounds.

17. The method of claim 13, wherein the subject in need thereof is a human.

18. The method of claim 13, wherein the pharmaceutical composition comprises:
5-7 wt-% N,N$^1$-bis (2-hydroxyethyl) nonanediamide;
30-60 wt-% glycerol;
0.02-1 wt-% 2-dodecenedioic acid;
0-5 wt-% mucopolysaccharide;
0-1 wt-% hyaluronic acid;
0-15 wt-% *Echinacea purpurea* extract;
0-1 wt-% *Usnea barbata* extract;
0-1 wt-% phytosphingosine; and
0-0.2 wt-% bronopol.

19. The method of claim 13, wherein the pharmaceutical composition further comprises a buffer, a thickening agent, an emulsifier, or a mixture thereof.

20. The method of claim 13, wherein the composition has a form suitable for topical administration.

21. The method of claim 20, wherein composition is in the form of a thickened solution, a spray, a foam, an ointment, a cream, a gel, a medicated gauze, or a polyacrylamide based dressing.

* * * * *